(12) United States Patent
Ziaee

(10) Patent No.: US 6,626,177 B1
(45) Date of Patent: *Sep. 30, 2003

(54) NASAL MASK

(76) Inventor: Saeed Ziaee, 255 Duncan Mill Rd., Suite 510, Don Mills (CA), M3B 3H9

( * ) Notice: Subject to any disclaimer, the term of this patent is extended or adjusted under 35 U.S.C. 154(b) by 0 days.

This patent is subject to a terminal disclaimer.

(21) Appl. No.: 09/593,813

(22) Filed: Jun. 15, 2000

Related U.S. Application Data

(60) Provisional application No. 60/139,721, filed on Jun. 18, 1999.

(51) Int. Cl.[7] ............................................. A62B 18/02
(52) U.S. Cl. .............................. 128/206.21; 128/206.24
(58) Field of Search ...................... 128/206.21–207.11, 128/207.13, 206.11, 206.12, 206.13, 206.14, 206.16–206.19, 207.18, 205.25

(56) References Cited

U.S. PATENT DOCUMENTS

| | | | | |
|---|---|---|---|---|
| 1,362,766 A | * | 12/1920 | McGargill ................... 128/140 |
| 2,663,297 A | * | 12/1953 | Turnberg ................ 128/207.18 |
| 3,902,486 A | * | 9/1975 | Guichard ..................... 128/140 |
| 4,248,218 A | * | 2/1981 | Fischer ................... 128/204.18 |
| 4,782,832 A | * | 11/1988 | Trimble et al. ......... 128/207.18 |
| 4,811,730 A | * | 3/1989 | Milano ................... 128/203.11 |
| 4,944,310 A | * | 7/1990 | Sullivan ..................... 128/848 |
| 4,996,983 A | * | 3/1991 | AmRhein .............. 128/206.11 |
| 5,042,478 A | * | 8/1991 | Kopala et al. .......... 128/207.18 |
| 5,113,857 A | * | 5/1992 | Dicketman et al. .... 128/207.18 |
| D333,015 S | | 2/1993 | Farmer .......................... D29/8 |
| 5,477,852 A | * | 12/1995 | Landis et al. ........... 128/207.18 |
| 5,538,000 A | * | 7/1996 | Rudolph ................. 128/205.25 |
| 5,647,357 A | * | 7/1997 | Barnett et al. .......... 128/206.24 |
| 5,687,715 A | * | 11/1997 | Landis et al. ........... 128/207.18 |
| 5,724,965 A | | 3/1998 | Handke .................. 128/207.13 |
| D402,755 S | | 12/1998 | Kwok ..................... D24/110.4 |
| 5,884,624 A | * | 3/1999 | Barnett et al. .......... 128/206.24 |
| 6,019,101 A | * | 2/2000 | Cotner et al. ........... 128/207.13 |
| 6,035,852 A | * | 3/2000 | Hoftman ................ 128/206.26 |
| D423,096 S | * | 4/2000 | Kwok ..................... D24/110.1 |
| 6,112,746 A | * | 9/2000 | Kwok et al. ............ 128/207.13 |
| 6,123,071 A | * | 9/2000 | Berthon-Jones et al. ...................... 128/204.18 |
| 6,135,109 A | * | 10/2000 | Blasdell et al. ......... 128/206.28 |
| 6,263,874 B1 | * | 7/2001 | LeDez et al. ........... 128/206.21 |
| 6,397,847 B1 | * | 6/2002 | Scarberry et al. ....... 128/206.24 |
| 6,431,172 B1 | * | 8/2002 | Bordewick ............. 128/207.18 |
| 6,467,483 B1 | * | 10/2002 | Kopacko et al. ........ 128/207.12 |

* cited by examiner

*Primary Examiner*—Weilun Lo
*Assistant Examiner*—Teena Mitchell
(74) *Attorney, Agent, or Firm*—Grossman & Flight LLC

(57) ABSTRACT

A nasal mask has a shell portion that is a hollow enclosure with a rearwardly facing opening that is defined by edge portions of the shell portion. A resiliently deformable endless interface member engages and extends around the edge portion of the opening and forms a seal between the shell portion and the user's face. The shell portion and the interface member are generally symmetrical about a median place. The shell portion has two gas inlet orifices, one on each side of the median place. Each orifice is provided with an outwardly extending tubular portion for engaging a gas inlet tube.

20 Claims, 5 Drawing Sheets

NASAL MASK

CROSS-REFERENCE TO RELATED APPLICATIONS

This application claims the benefit of the filing date of provisional application No. 60/139,721 filed Jun. 18, 1999.

BACKGROUND OF THE INVENTION

The present invention relates to a nasal mask. Known nasal masks of which the applicant is aware have suffered from various disadvantages. For example, known nasal masks do not prevent leakage of gas such as air or oxygen from the mask efficiently, and do not distribute forces evenly on the face of the user. With known masks, an undesirably high tensile force has to be exerted by the straps or other mask retaining devices that hold the mask to the user's head, and as a result excessive pressure tends to be exerted on the user's face, causing breakdown of the skin, for example, on the bridge of the nose. Further, known masks interfere with use of eye glasses while wearing the mask, and may present the difficulty that a gas tube may become pinched or obstructed when the user lies on one side, for example when the user is sleeping.

BRIEF SUMMARY OF THE INVENTION

The present invention provides a shell portion and an interface member for a nasal mask comprising a shell portion defining a hollow enclosure with a rearwardly facing opening defined by edge portions of the shell portion, and a resiliently deformable endless interface member engaging with and extending around said edge portion of the opening and adapted to form a seal between the shell portion and the user's face, and wherein the shell portion and the interface member are at least generally symmetrical about a median plane, and said shell portion has two gas inlet orifices disposed one on each side of the median plane. With this arrangement, the mask may be supplied with gas through two relatively small diameter flexible tubes coupled to the orifices, respectively. The small diameter tubes exert only relatively small tensile forces away from the user's face, and therefore only relatively small forces need to be exerted by retaining straps to retain the mask, and as a result, excessive application of force to the user's face and problems such as breakdown of skin on the bridge of the nose can be avoided. Further, the smaller tubes can be easily oriented in any desired position relative to the mask. For example, they may be positioned downwardly below the mask to facilitate wearing of eye glasses, or may be positioned centrally of the top of the user's head so that they are not obstructed if the user lies on one side.

In a preferred form, the gas inlet orifices are positioned symmetrically with respect to the median plane, and the inner side of the shell adjacent each orifice is provided with an inwardly extending tubular portion for engaging deformable nasal pillows that may form a seal between each orifice and a nostril of the user.

Preferably, the edge portions defining the rearwardly facing opening of the shell are re-entrant edge portions so that the pressures within the mask tend to provide a rearwardly directed component of force tending to resist movement of the mask away from the face of the user. This allows the force applied by the retaining devices to be still further decreased, so that the effects of pressure on the skin of the face of the user may be further alleviated.

Preferred embodiments of the present invention will now be described in more detail, by way of example only, with reference to the accompanying drawings.

DETAILED DESCRIPTION OF THE INVENTION

Figure 1:
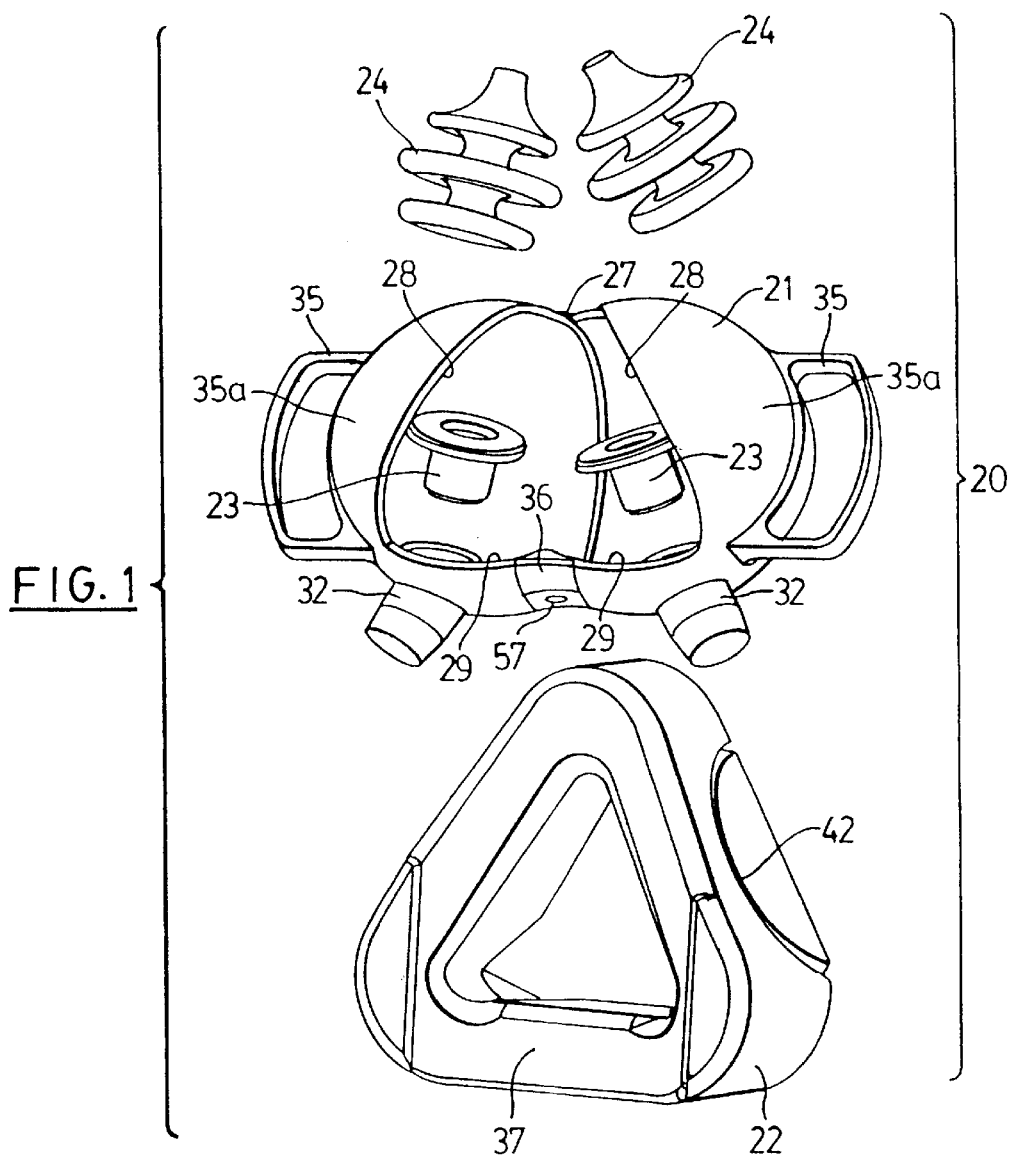
FIG. 1 shows an exploded view form the rear of a nasal mask in accordance with the invention.

Referring to the drawings wherein like reference numerals indicate like parts, a mask 20 comprises a shell portion 21 and an interface portion 22, preferably used in combination with pillow engaging members 23 and nasal pillows 24.

Figure 4A:
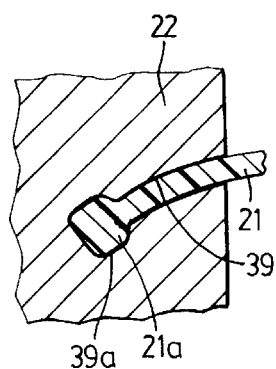
FIG. 4a is a partial cross-sectional view on an enlarged scale showing a modification of the structure of FIG. 4.
Figure 4:
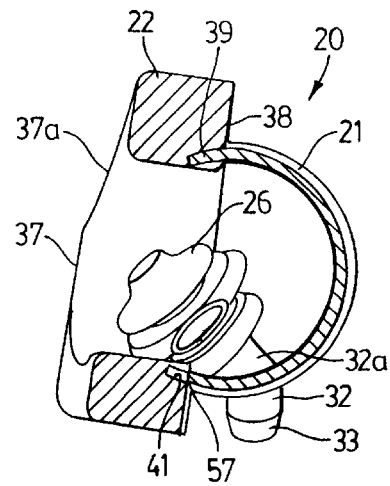
FIG. 4 shows a cross-sectional view taken on the line 4—4 in FIG. 3.
Figure 5:
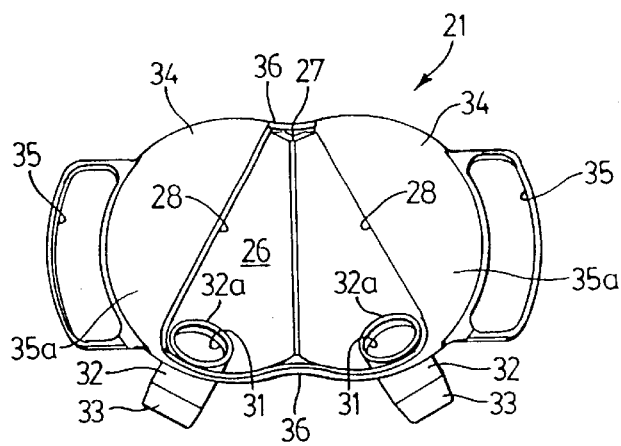
FIG. 5 is a view from the rear of the shell portion of the mask.

As best seen in FIGS. 1, 2, 4 and 5 shell portion 21 defines a hollow enclosure with a rearwardly facing generally triangular opening 26 defined by edges of the shell comprising a transverse top portion 27, arcuately transversely outwardly and downwardly extending side portions 28 and arcuate lower edge portions 29. The shell 21 is generally symmetrical about a median plane .3 seen in FIG. 2, and the shell portion 21 has two gas inlet orifices comprising openings 31 in the lower front portion of the shell 21. Adjacent each opening 31, the shell 21 is formed integrally with outwardly extending tubular portions 32 having slightly tapering end portions 33 defining a flow passage extending from the outer end of the tubular portions to the interior of the shell 21 through the openings 31. In the preferred form, inwardly of the shell 21 and integrally formed therewith are inwardly extending tubular portions 32a that, as seen in FIG. 4, each have their axes inclined somewhat downwardly rearwardly with respect to the axis of the outwardly extending portion 32.

In the preferred form, shell 21 comprises two part spherical portions 34 that are connected together along a bridging portion 36 coincident with the median plane. The spherical portions 34 provide especially good symmetry and distribute pressure evenly on the wearer's face and provide reentrant portions providing rearwardly directed forces urging the mask toward the wearer's face.

Each portion 34 has on each transversely outer side, at a portion intermediate the front and rear sides of the shell 21, an integrally formed strap lug 35 to which a retaining strap may be attached.

The shell portion 21 may, for example, be molded of a rigid plastics material.

The interface member 22 is preferably formed of a soft, compliant and resiliently deformable material, for example a soft silicone rubber composition that provide a cushion between the rigid shell 21 and the patient's face ;and conforms to and seals to the patient's face on the one hand and to the shell 21 on the other.

Figure 6:
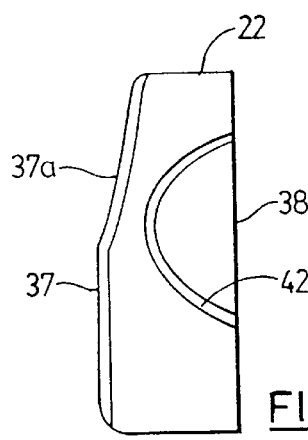
FIG. 6 is a side view of the interface portion of the mask.
Figure 7:
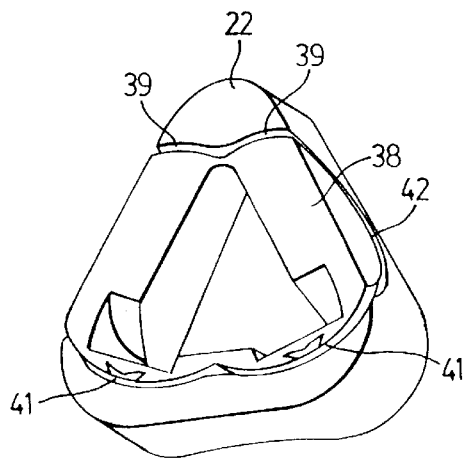
FIG. 7 is an isometric view from the front of the interface portion.

As best seen in FIGS. 1, 6 and 7, the interface 22 comprises a generally triangular endless member with rounded corners and generally planar rear and front sides 37 and 38 that, in use, engage with the patient's face and with the shell 21, respectively. As seen in FIG. 4, the rear side 37 of the interface member 22 may incline slightly forwardly upwardly at 37a, so that the member 22 tapers slightly in thickness upwardly and tends to conform to the patient's cheeks on each side of the nose.

Figure 2:
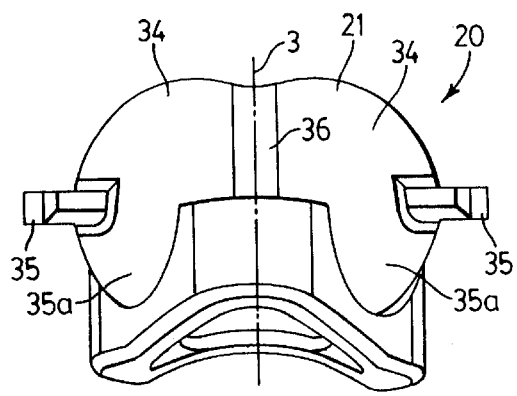
FIG. 2 is a top plan view of the mask of FIG. 1 in assembled condition.
Figure 3:
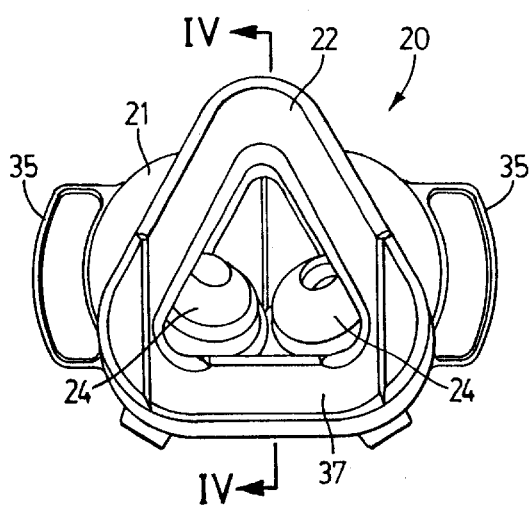
FIG. 3 is a view from the rear of the mask in the assembled condition.

The upper portion of the front side 38 of the interface member 22, as best seen in FIG. 7 is formed with a series of part circular grooves that receive the edges of the shell portion 21 when the interface is applied to the shell portion in the assembled condition as seen in FIGS. 2 to 4. As best seen in FIG. 7, these grooves are symmetrical about the median plane and comprise upper part circular grooves 39 that receive the bridge portion 36 and upper portions of the edges 28, and lower part circular grooves 41 that receive the lower edges 29 and lower portions of the side edges 28. Further, the sides of the interface portion 22 are formed with part circular grooves 42 that receive the intermediate portions of the side edges 28.

As best seen in FIG. 4, the grooves preferably penetrate a depth of at least about 25% of the thickness of the interface 22. Preferably, the grooves are slightly narrower than the thickness of the shell 21, so that there is a resilient reaction tending to cause the sides of the grooves to grip tightly on the edges of the shell 21. As shown in FIG. 4a, the edges of the shell 21 may be formed with a thickened bead 21a, and the bottom of each of the grooves such as groove 39 in the interface 22 may be formed with an enlarged recess 39a of somewhat smaller dimensions than the bead 21a, so that there is a resilient reaction tending to cause the material of the interface 22 to grip resiliently on the enlarged bead 21a, and improve the security of attachment of the interface 22 to the shell 21.

It will be noted that the interface member 22 is removably connected to the shell portion 21 so that it can be detached and a somewhat smaller or larger interface member substituted, in order to improve the fit of the interface member to the face of the patient.

Optionally, the mask may be used with nasal pillows 24 that are mounted on pillow engaging members 23. However, the use of such nasal pillows is not essential, and it is contemplated the mask may be used without such nasal pillows.

Figure 10:
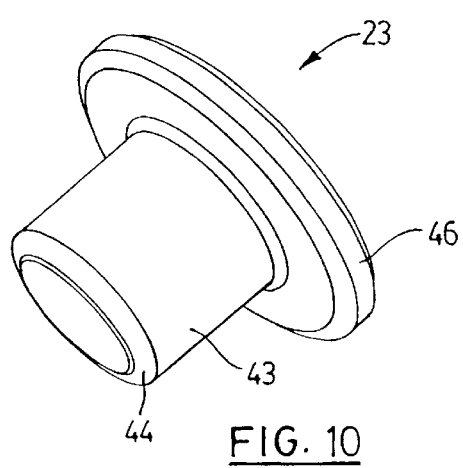
FIG. 10 is an isometric view from the rear and below of a disk member optionally forming part of the mask.
Figure 11:
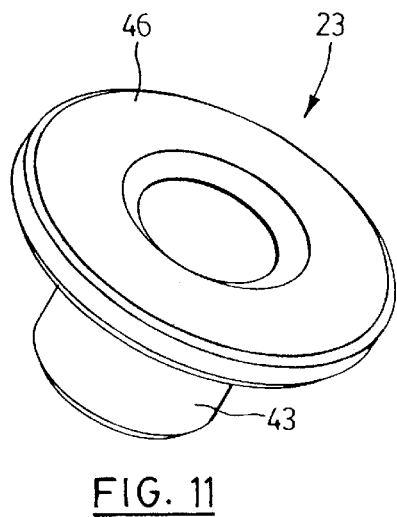
FIG. 11 shows an isometric view from above and from one side of the disk member.

As seen in FIGS. 10 and 11, the pillow engaging members 23, which may be molded of rigid plastics material, comprise hollow cylindrical stem portions 43 with tapering lower ends 44, and formed integrally with an enlarged disk element 46.

Figure 8:
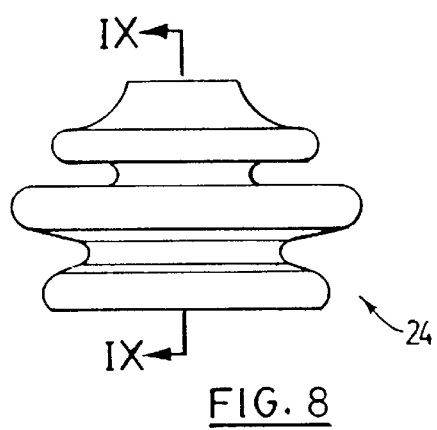
FIG. 8 is a side view of a nasal pillow optionally forming a portion of the mask.
Figure 9:
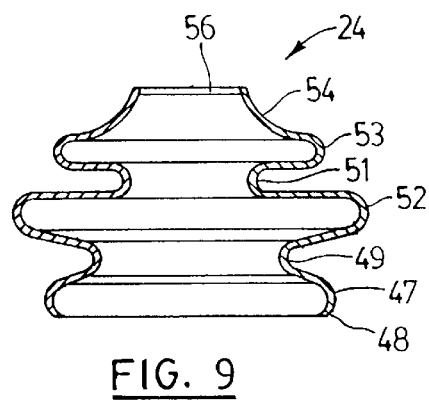
FIG. 9 is a cross-section along the line 9—9 in FIG. 8.

The nasal pillows 24, as best seen in FIGS. 8 and 9 re preferably formed of a highly resiliently deformable oft plastics material, for example soft silicone rubber composition.

The pillow is of a generally corrugated or accordion-pleated structure have a wide base portion 4 7 with re-entrant lower edges 48, relatively narrow intermediate portions 49 and 51, and relatively wide portions 52 and 53, the upper most of these terminating in an upwardly arcuately tapering tip 54 having a circular opening 56 at the upper edge.

In use, a disk element 46 of a member 23 is inserted within one of the wider portions 48, 52 or 53 of the nasal pillow 24 by stretching the material of the pillow 24, so that the disk element 46 snap-fits within one of the wider portion. The nasal pillows together with the members 23 are then inserted within the mask, and the stem portions 43 inserted within the inwardly extending cylindrical tubular portions 32a of the shell 21, as seen in FIGS. 3 and 4. The position of the pillows 24 within the mask may be adjusted to enable the tapering tip portions 54 of the pillows to engage snugly and in a leak free manner within the nostrils of a patient. This adjustment is effected by engaging the disk element 46 with a higher or with a lower one of the wider portions. 47, 52 or 53.

Desirably, the shell 21 is provided with a small vent hole 57 in a lower portion of the bridge portion 36 of the shell, so that excessive pressure does not build up within the shell 21, for example when the mask 20 is applied and tightened to the user's face. If desired, this hole 57 may be plugged with a tight-fitting resilient e.g. rubber plug.

Figure 12:
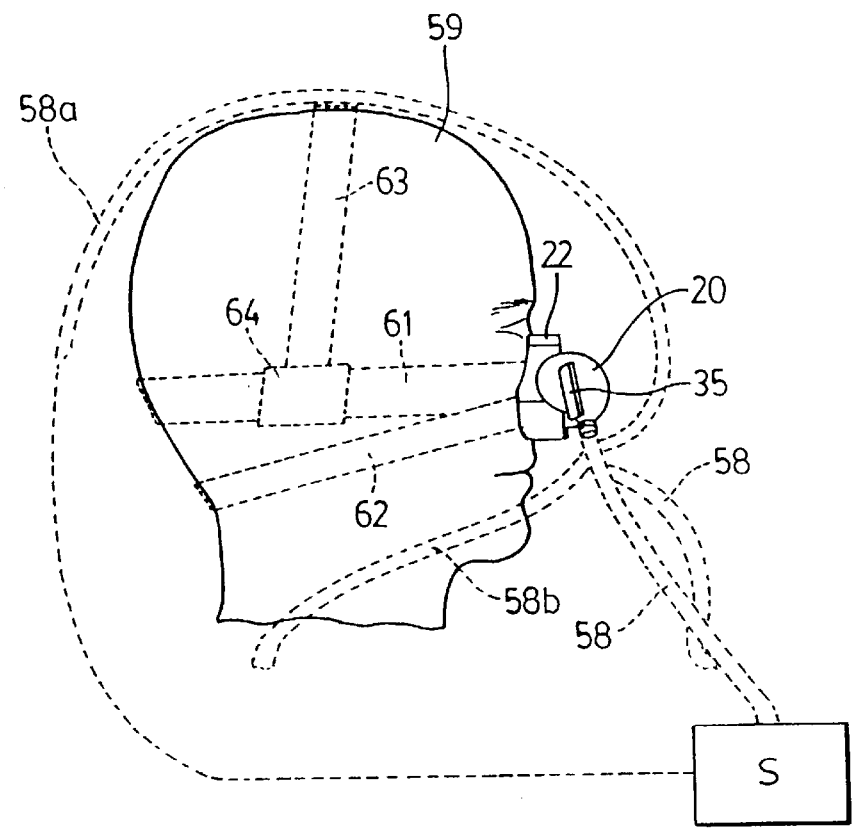
FIG. 12 shows somewhat schematically the mask worn by a patient.

In use, as seen in FIG. 12, a relatively small diameter gas or air supply hose 58 is push fitted over each outer cylindrical tubular portion 32, as shown in broken lines in FIG. 12, and is connected to a source S of air or other gas to be supplied to the patient. A strap or straps are attached through the strap lugs 35, and are passed around the head 59 to retain the mask 20 with the interface 22 pressed firmly and in a leak free fashion against the bridge of the nose, upper lip and cheeks on either side of the nose as seen in FIG. 12. Preferably, as seen in FIG. 12, the straps comprise a first strap 61 passing around the back of the patient's head 59, a second strap 62 passing around the head 59 at a region lower than strap, and a third strap 63 connected to intermediate portions 64 of strap 61 on each side of the patient's head 59 and passing over the top of the head 59. The straps 61 to 63 are usually resilient and may incorporate buckles or the like whereby the tension in each strap may be adjusted.

The relatively small diameter tube 58 exert only relatively small tensile forces in the direction away from the face of the patient and therefore only relatively small forces need to be exerted by the straps 61 and 62 to retain the mask 20 and, as a result, excessive application of force to the user's face can be avoided. Pressure differentials over ambient existing in the inside of the shell 21 tend to bias the mask 20 toward the user's face as a result of the reaction of the pressure against the re-entrant portions 35a of the shell that extend rearwardly transversely inwardly between the lugs 35 and the edges 28 of the opening 26, so that excessive force exerted by the strap 59 can be avoided without risking leaks from the mask. The small diameter tubes may be easily oriented in any desired position relative to the mask 20. For example, they may be positioned downwardly below the mask as indicated for the tubes 58 in FIG. 12, they may be positioned centrally of the top of the user's head, as indicated by reference numeral 58a in FIG. 12, so that they are not obstructed if the user lies on one side, for example, when sleeping, or they may pass rearwardly on one side or on each side of the patient's head 59, as indicated by reference numeral 58b in FIG. 12, to a source placed behind the user.

When the nasal pillows 24 are employed, an especially leak free delivery of gas to the patient's airways can be provided, so that gas supplied at a selected pressure from the source S can be delivered to the patient without leaks and pressure loss occurring.

What is claimed is:

1. A shell for a nasal mask, comprising:
a shell portion defining a hollow enclosure with a rearwardly facing opening defined by re-entrant edge portions of the shell portion, said re-entrant edge portions extending transversely inwardly and rearwardly from an intermediate portion of the shell toward said rearwardly facing opening, and wherein the shell portion is at least generally symmetrical about a median plane, and said shell portion having two gas inlet orifices disposed one on each side of the median plane.

2. The shell as claimed in claim 1 wherein the gas inlet orifices are positioned symmetrically with respect to said median plane.

3. The shell as claimed in claim 1 wherein adjacent each orifice the shell portion is formed integrally with an outwardly extending tubular portion defining a flow passage through said orifice.

4. The shell as claimed in claim 3 wherein each tubular portion has a tapering end portion.

5. A shell as claimed in claim 1 wherein said shell portion has an outer side, the shell further comprising two lugs for receiving a strap disposed, one lug on each side of the median plane, and integrally formed on said outer side.

6. A shell as claimed in claim 1 molded from a rigid plastics material.

7. In combination, the shell as claimed in claim 1 and a pair of resiliently deformable nasal pillows adapted to be received in the nostrils of a wearer of the mask, and a pair of pillow engaging members each adapted to connect between a gas inlet orifice of said shell portion and a respective pillow.

8. The combination of claim 8 wherein each pillow engaging member comprises a disk member, and each pillow is generally tubular and corrugated and comprises a tapering tip, a plurality of relatively narrow intermediate portions and a plurality of relatively wide intermediate portions, whereby a height of the tip within the shell can be adjusted by engaging the disk member in a selected relatively wide intermediate portion of the pillow.

9. The combination of claim 8 wherein adjacent each gas inlet orifice the shell portion is formed integrally with an inwardly extending tubular portion defining a flow passage through said orifice.

10. The combination of claim 9 wherein each pillow engaging member comprises a hollow cylindrical stem portion adapted to be received in said inwardly extending tubular portion.

11. A nasal mask comprising a shell as claimed in claim 1 and a resiliently deformable endless interface member engaging with and extending around said re-entrant edge portions defining the opening of said shell portion and adapted to form a seal between the shell portion and a user's face, and wherein the interface member is at least generally symmetrical about a median plane.

12. A mask as claimed in claim 11 wherein said rearwardly facing opening and said endless interface member are each generally triangular.

13. A mask as claimed in claim 11 wherein the interface member is removably connected to the shell portion.

14. A mask as claimed in claim 11 wherein said interface member is provided with grooves that receive said re-entrant edge portions of said shell portion defining said opening.

15. A mask as claimed in claim 14 wherein said interface member has an interior wall and an exterior wall, the distance between said interior wall and said exterior wall being a thickness, and wherein said grooves penetrate at least 25% the thickness of the interface member.

16. A mask as claimed in claim 15 wherein said grooves are narrower than the thickness of the shell.

17. A mask as claimed in claim 14 wherein each of said re-entrant edge portions is provided with an edge bead adapted to be received in an enlarged recess within said grooves.

18. An interface member for a nasal mask, said interface member comprising a generally triangular, resiliently deformable endless member having grooves in a generally planar face and in adjacent sides thereof adapted to receive re-entrant edge portions of a shell portion, and wherein said endless member and the grooves therein are at least generally symmetrical about a median plane.

19. An interface member as claimed in claim 18 further comprising a user-engaging face spaced apart from said planer face, and wherein said grooves penetrate at least 25% of a thickness of the interface member recessed between said planar face and said user-engaging face.

20. An interface member as claimed in claim 18 wherein a base of each groove defines an enlarged recess adapted to receive an edge portion having an enlarged edge bead.

* * * * *